United States Patent
Schmit et al.

(10) Patent No.: US 10,210,721 B2
(45) Date of Patent: Feb. 19, 2019

(54) ACTIVE ECG LEAD QUALITY INDICATION AT THE POINT OF CARE

(71) Applicant: General Electric Company, Schenectady, NY (US)

(72) Inventors: Rodger F. Schmit, Wauwatosa, WI (US); Adrian F. Warner, Wauwatosa, WI (US); Daniel R. Schneidewend, Wauwatosa, WI (US); Timothy P. Stiemke, Wauwatosa, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 15/373,954

(22) Filed: Dec. 9, 2016

(65) Prior Publication Data
US 2018/0165923 A1 Jun. 14, 2018

(51) Int. Cl.
*A61B 5/0408* (2006.01)
*G08B 5/36* (2006.01)
(Continued)

(52) U.S. Cl.
CPC .......... *G08B 5/36* (2013.01); *A61B 5/04085* (2013.01); *A61B 5/6843* (2013.01); *G01R 19/04* (2013.01); *G01R 27/02* (2013.01)

(58) Field of Classification Search
CPC ..... G08B 5/36; A61B 5/04085; A61B 5/6843; G01R 27/02
(Continued)

(56) References Cited

U.S. PATENT DOCUMENTS 5,042,498 A   8/1991   Dukes
5,819,741 A   10/1998  Karlsson et al.
(Continued)

FOREIGN PATENT DOCUMENTS

| EP | 0450350 | 10/1991 |
|----|---------|---------|
| WO | 2008056309 | 5/2008 |
| WO | 2013074114 | 5/2013 |

OTHER PUBLICATIONS

Farrell et al., "Effect of Lead Quality on Computerized ECG Interpretation", Computers in Cardiology, vol. No. 31, pp. 173-176, retrieved from http://www.cinc.org/archives/2004/pdf/173.pdf, Oct. 2004.

*Primary Examiner* — Firmin Backer
*Assistant Examiner* — Munear Akki
(74) *Attorney, Agent, or Firm* — GE Global Patent Operation; Marc A. Vivenzio

(57) ABSTRACT

In the present invention, an electrophysiology (EP) mapping or recording device for obtaining and recording information on a patient connected to the EP system includes a central processing unit (CPU), a display connected to the CPU, a cable lead connected to the CPU and configured to supply a physiological signal to the CPU from an electrode disposed on a patient, such as an electrocardiogram (ECG) surface electrode. A signal quality indication system includes a CPU capable of determining the EC signal quality and a light source disposed on the cable lead in close proximity to the patient. The light source is operated by the CPU to emit light in varying colors and/or in varying intensities or configuration corresponding to the quality of the physiological signal to visually represent the presence and quality of the physiological signal on the cable lead.

19 Claims, 3 Drawing Sheets

(51) Int. Cl.
*A61B 5/00* (2006.01)
*G01R 27/02* (2006.01)
*G01R 19/04* (2006.01)

(58) Field of Classification Search
USPC .............. 340/539.12, 539.13, 691.8, 636.12; 600/509
See application file for complete search history.

(56) References Cited

U.S. PATENT DOCUMENTS

| | | | |
|---|---|---|---|
| 7,340,294 B2 | 3/2008 | Gray | |
| 8,112,140 B2* | 2/2012 | Graβl | A61B 5/04085 600/382 |
| 8,805,482 B2 | 8/2014 | Sitzman et al. | |
| 2003/0083584 A1* | 5/2003 | Yonce | A61B 5/0424 600/509 |
| 2008/0027338 A1* | 1/2008 | Lu | A61B 5/0424 600/509 |
| 2013/0030482 A1 | 1/2013 | Warner et al. | |
| 2015/0011901 A1 | 1/2015 | Warner et al. | |
| 2015/0250554 A1* | 9/2015 | Young | A61B 5/0408 600/372 |
| 2017/0215247 A1* | 7/2017 | Weaver | H05B 33/0869 |

* cited by examiner

ACTIVE ECG LEAD QUALITY INDICATION AT THE POINT OF CARE

BACKGROUND OF INVENTION

The invention relates generally to indication systems for cable leads, and more particularly to identification systems that enable the signal strength or quality for cable leads to be visually represented on the cable leads during studies or monitoring of patients.

Electrocardiography (ECG) studies record the electrical activity and pathways of a heart to identify, measure and diagnose arrhythmias. In particular, such studies measure electrical changes caused by the depolarization of the heart muscle during each heartbeat. To accomplish this, ECGs utilize electrodes that are combined into combinations, the output of which are referred to as a lead.

ECG leads are used in electrophysiology (EP) studies, which assess electrical activity through the use of catheters placed in the heart through veins or arteries. More specifically, surface ECG leads attached to the patient are used as the reference for the intra cardiac signals from the catheters. That is, they provide a voltage reference to the patient for measurement by other leads.

For EP recorder devices in general there is a strong reliance for the signal formation on the surface leads relative to the Wilson Central terminal. Thus, any degradation in the quality of the signal from the patient from the electrode, through the lead wire, the block and trunk cable can affect the intra-cardiac channels negatively with the imposition of noise on the wanted signal. An important mitigation for this is to ensure good electrode contact thus good signals from the electrode to the EP device.

In this context, ECG leads may encounter noise from a variety of sources such as power lines and wireless electrical devices. Moreover, EP studies are typically combined with ablation therapy in which a catheter employs radiofrequency energy, for example, to treat arrhythmias. Various medical devices may also attached to a patient during an EP study potentially creating noise. In addition, ECG leads have to measure relatively small electrical signals from the patient, less than 20 uV in some instances. As will be appreciated, given the above considerations, achieving acceptable study recordings may be challenging.

One significant problem in the utilization of the ECG in EP studies is physician awareness of the quality of the electrode site relative to the surface leads, and more importantly their impact on the intracardiac lead formation. While error messages on the screen of the monitoring device to which the surface leads are attached are a very logical solution to address this, the physician work space by necessity is already complex. Thus, any warning messages on the monitor screen, and additional demands on the user can be counterproductive.

Further, typically degradation of the electrode site occurs over a long period of time. Whereas loss of contact happens quickly, i.e., a bad lead, or disconnect from the electrode tab, which can be readily apparent either on the patient (disconnect) or on the monitor (warning of loss of signal from bad lead) intermittent signal behavior is not as readily noticeable and can easily be overlooked.

In addition, this challenge increases exponentially with complex patient studies such as performed in cardiac electrophysiology where catheter/lead sets of up to 250+ individual catheters/leads are possible, such as when using complex mapping catheters. In these situations, it is often difficult to locate a non-functional or reduced functioning lead which can cause significant issues, including a misdiagnosis of the patient.

There are many pre-existing solutions to electrode quality determination such as PCT Application No. WO/2008/056309A3, entitled ECG Electrode Contact Quality Measurement System. However, while references of this type can determine the quality of the signal received by the electrode, the manner in which these determinations are conveyed to the physician remain the same, i.e., a warning or error message on an EP recorder screen, which is often lost in the midst of all other information being displayed on the screen, or an audible alert, which can often be thought or as distracting and can be lost in other sounds provided by the EP recorded or other devices within the area in which the procedure is being performed. As such, any conveyance of an error message related to the signal quality needs to be done in a more direct and readily-assimilated manner.

In one prior art attempt to solve this issue, U.S. Pat. No. 5,042,498, entitled Intelligent Electrocardiogram System, which is expressly incorporated herein by reference in its entirety for all purposes, discloses an electrode for use with an ECG system or instrument that includes an LED incorporated within the electrode structure. The LED is operably connected to the device, such that when a difference in the impedance between the patient and the electrode is detected, the system activates the LED to identify the faulty electrode.

While capable of identifying the particular electrode that is malfunctioning, the LED utilized on this electrode provides only rudimentary information concerning the electrode function, and nothing concerning the quality of the cable lead or the signal from the patient being transmitted via the cable lead.

Accordingly, it is desirable to develop a visual indication system and method for the indication of the quality of a signal from an ECG lead at the patient, with the indication providing visual information regarding the signal as well as changes in the signal during the study utilizing the indication system.

BRIEF DESCRIPTION OF THE INVENTION

There is a need or desire for an indication system to visually identify the state of a signal received or transmitted by an ECG surface lead on the patient. The above-mentioned drawbacks and needs are addressed by the embodiments described herein in the following description.

According to one exemplary aspect of the invention, a signal or lead quality detection and indication system for a surface electrode includes one or more patches or electrodes adapted to be placed on the skin or surface of a patient. The electrodes are connected to cable leads that extend from the electrodes to an electrocardiogram (ECG) or electrophysiological (EP) or other monitoring, recording or mapping device or system, such that signals being received from or sent to the electrodes can be monitored by the device.

Each of the cable leads includes a number of indicators, such as a light emitting diode (LED), disposed directly on the lead or in association with the lead. When a cable lead is connected to the monitoring, recording or mapping device or system, a central processing unit (CPU) for the display on the device can monitor the signal, e.g., the impedance, transmitted by the cable lead to the device. The signal form the cable lead is compared with a reference signal in order to determine the quality of the signal. This can include the determination of any noise in the signal, the lack of a signal, or any other suitable determination made regarding the quality of the signal transmitted along the cable lead. Depending upon the quality determined, the device can operate one or more indicators disposed on the cable lead to provide a visual indication of the quality of the signal. The ability to provide an indication of the error or fault at the location of the cable lead/electrode is significant because the cable lead is in the direct vicinity of the patient being viewed/treated by the physician. As such a change in the state of the indicators at that location can be readily observed and assimilated by the physician.

According to another aspect of an exemplary embodiment of the invention, in conjunction with the indicators on the cable lead providing an analog translation of impedance change into a color change at the patient to heighten awareness of the consequential impact, other forms of messaging, supplemental analysis windows and the like can all be utilized in conjunction with the indicators on the cable lead to provide redundancy to the conveyance of the relevant information.

According to still another aspect of an exemplary embodiment of the invention, as the quality of the signal changes over time, the device can actively or constantly monitor the lead impedance in order to determine the significance or amount of any changes to the signal. These differences can then be visually represented or indicated by alterations in the operation of the one or more indicators on the cable lead, thereby providing an indication of the signal quality directly on the cable lead. With transitional indicators of various types that are able to provide information beyond a rudimentary Go/No-Go red LED, for example, as covered in some prior art, the user can be provided with this additional information and control. Given that in EP studies subtle degradation in one area, i.e., the signals obtains/sent by surface ECG electrodes, significantly impacts other areas, i.e., intracardiac signal analysis, this helps sensitize the user to the importance the surface electrodes play in the delivery of good signal quality for the entire case. In this manner, the device enables the user to not only determine the existence of a signal quality issue but take proactive steps to resolve those poor electrode signal pathway issues as and when they occur.

According to still another aspect of one exemplary embodiment of the invention, a signal quality indication system for actively indicating a signal quality associated with an electrocardiogram (ECG) signal transmitted via a cable lead and associated electrode operably connected to electrophysiology (EP) recording or mapping device includes a central processing unit (CPU) within the EP device capable of determining a signal quality of the ECG signal, a cable lead including a first connector at one end adapted to operably connect the cable lead to an electrode and a second connector at the opposite end adapted to connect the cable lead to the CPU within the EP recording or mapping device and an indicator disposed on the cable lead, wherein the indicator is operated by the CPU to emit light corresponding to a determined signal quality for the ECG signal.

According to still a further aspect of one exemplary embodiment of the invention, an EP device for obtaining and recording information on a patient connected to the EP system, includes an amplifier including an electrode cable lead connector, a computer operably connected to the amplifier and including a central processing unit (CPU) connected to the amplifier and a display connected to the CPU, at least one cable lead connected to the cable lead connector and configured to supply a physiological signal to the CPU via the input module and amplifier, wherein the CPU is configured to determine a signal quality for the physiological signal supplied by the at least one cable lead and an indicator disposed on the at least one cable lead, wherein the indicator is operated by the CPU to emit light corresponding to a signal quality for the physiological signal determined by the CPU.

According to still a further aspect of one exemplary embodiment of the invention, a method of providing an indication of a quality of an physiological signal transmitted between an electrode disposed on a patient and an electrophysiology (EP) recording or mapping device is provided including the steps of providing a signal quality indication system operably connected to a central processing unit (CPU) of the EP device, the signal quality indication system including a cable lead operably connected between the electrode and the CPU of the EP device, and a light source disposed in the cable lead and operably connected to the CPU, wherein the light source is operated by the CPU to emit light corresponding to a determination of the signal quality of the physiological signal, connecting the cable lead between the electrode and the CPU, determining the signal quality of the physiological signal transmitted by the cable lead; and operating the light source to emit a color corresponding to the determined quality of the physiological signal.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The drawings illustrate the best mode presently contemplated of carrying out the disclosure. In the drawings

DETAILED DESCRIPTION OF THE DRAWINGS

In the following detailed description, reference is made to the accompanying drawings that form a part hereof and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
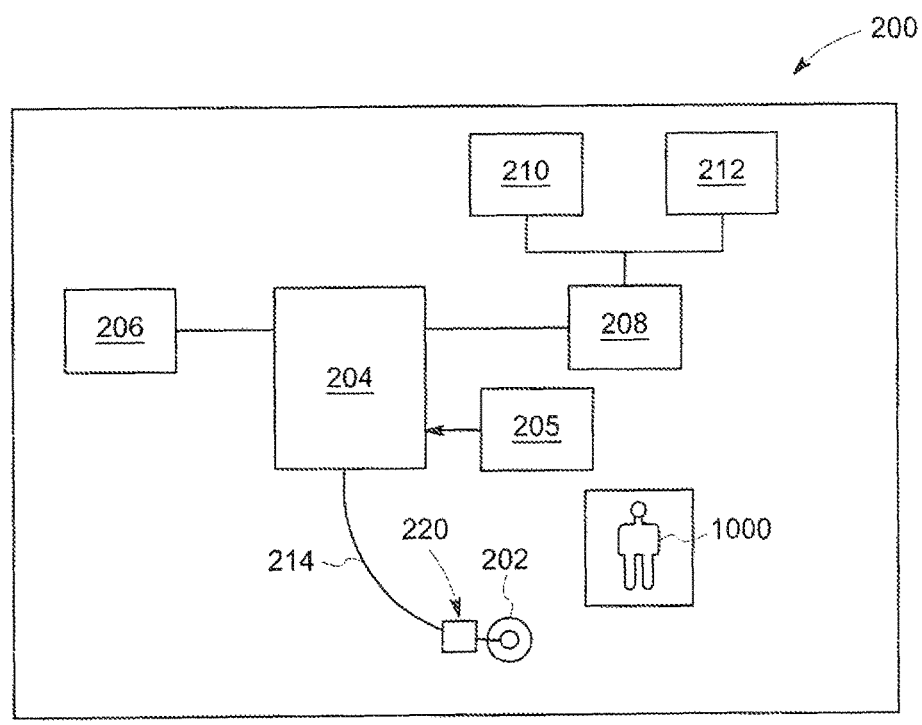
FIG. 1 is a schematic representation of an EP recording system including a signal quality indication system according to one exemplary embodiment of the present invention.

FIG. 1 illustrates one exemplary embodiment of an electrophysiology (EP) mapping or an EP recorder device or system 200, such as those used in intracardiac electrocardiography (ECG) studies within the body of a patient 1000. These devices or systems 200 apply/receive an electrical signal (e.g., electrical current) via one or more catheters 205 to various locations of the body of the patient 1000, such as the heart. The analysis of the signals sent and received by the catheters 205 is compared with reference signals obtained from a number of surface ECG electrodes 202 placed on the patient 1000. The system 200 can be similar to that disclosed in US Patent Application Publication No. US2013/0030482, which is expressly incorporated herein in its entirety. In the exemplary illustrated embodiment, the device or system 200 includes an amplifier 204 that is operably connected between a signal generator 206 and a suitable computer, including or formed as a controller or central processing unit (CPU) 208. In operation, signals generated by the signal generator 206 are transmitted to the catheter 205 by the amplifier 204. A return signal from the patient 1000, such as an ECG signal, is received by the amplifier 204 either via the catheter 205 or more often through the surface electrodes 202, and is processed by the amplifier 204 prior to transmitting the return signal to the CPU 208. The CPU 208 performs additional functions on the return signal and displays the information provided by the return signal on one or both of a real-time display 210 and a review display 212. The displays 210,212 illustrate the information obtained from the each of the various return signals in graphs, numbers or other manners with different colors to enable the clinician viewing the displays to readily distinguish the information provided by the various signals from one another.

Figure 2:
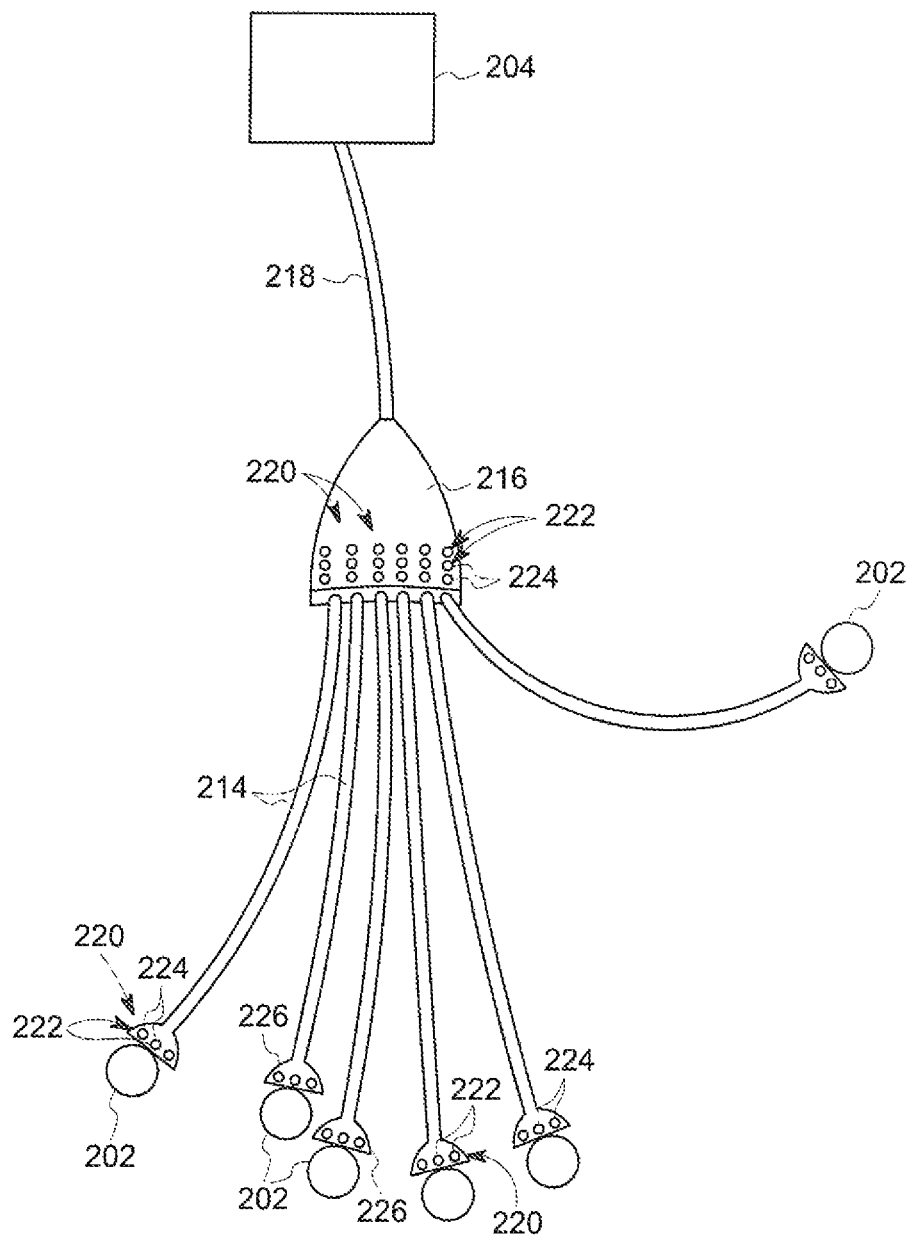
FIG. 2 is a schematic representation of a cable lead for the recording system of FIG. 1 according to an exemplary embodiment of the invention.

In the illustrated exemplary and non-limiting embodiment of FIGS. 1 and 2, each electrode 202 is connected to the amplifier 204 by a cable lead 214, The cable lead 214 can be connected to the electrode 202 in any suitable permanent or detachable manner, such as by spring loaded electrically-conductive clip (not shown) disposed on the lead 214 and selectively engageable with a contact (not shown) on the electrode 202, in a known manner. The cable lead 214 extends from the electrode 202 either for direct connection to the amplifier 204, or into connection with a harness 216. The harness 216 is to connected a number of cable leads 214 at one end and includes a single connection cable 218 opposite the leads 214 that is connected with the amplifier 204.

In either embodiment the cable lead 214 conducts the signals received by the electrodes 202 to the amplifier 204 for use in conducting the EP analysis in conjunction with the signals sent to the patient 100 via the catheter 205. The signals are continuously analyzed by the CPU 208, which can determine if there are any changes in the quality of the signal, e.g., the impedance of the signal resulting from the level of contact of the electrode 202 with the patient 1000, from each cable lead 214. The particular analysis or method of the analysis is not described in detail as a number of different manner for doing so are known in the art, including, but not limited to those disclosed in U.S. Pat. No. 7,340,492, entitled Impedance Measurement Apparatus For Assessment Of Biomedical Electrode Interface Quality, and U.S. Pat. No. 8,805,482 entitled System And Method For Signal Quality Indication And False Alarm Reduction In ECG Monitoring Systems, each of which are expressly incorporated herein by reference in their entirety for all purposes. Further, regardless of the specific analysis utilized to determine signal quality, the device or system 200 enables the user to define thresholds or set points for the degradation of the signal that trigger various levels of response from the device or system 200. The end points between perfect connectivity of the electrode 202 with the patient 1000 and complete disconnection of the electrode 202 from the patient 1000, i.e., an open circuit, are fixed for the analysis. However, the transition or threshold point or points between these end points, such as based on the noise level present in the signal being analyzed, are user selectable allowing the degree of user sensitivity to the degradation of contact of the electrode 202 and resulting signal impedance to be under user control.

In performing the analysis of the signal quality, the CPU 208 can communicate this result in a highly direct manner to the physician by operating one or more indicators 220 that are disposed on the cable lead 214. The indicators 220 can take any suitable form, but the illustrated exemplary and non-limiting embodiments of FIGS. 1 and 2, the indicators 220 are formed as one or more light sources 222 disposed on the cable head 226 for each cable lead 214 connected to and adjacent the associated electrode 202 and/or on the harness 216 in alignment with each of the cable leads 214 connected thereto. In this manner, each lead 214 connected to an electrode 202 for receiving and/or transmitting signals, such as, for example, the I-III, aVR-aVL, VI-6, and RL signals, includes indicators 220 associated with the signals being received from each electrode 202. The light sources 222 in one exemplary embodiment are formed as one or more multicolor LEDs 224 that enable the light sources 222 to provide a variety of indications to the physician regarding the signal quality for the particular cable lead 214 based on the different colors that can be projected by the light sources 222. The positioning of the light sources 222 on the cable lead 214 adjacent the electrode 202 or on the harness 216, or anywhere else on the cable lead 214, enables the physician to easily and readily view the information provided by the light sources 222 without having to look away from the patient to any appreciable extent.

Figure 3:
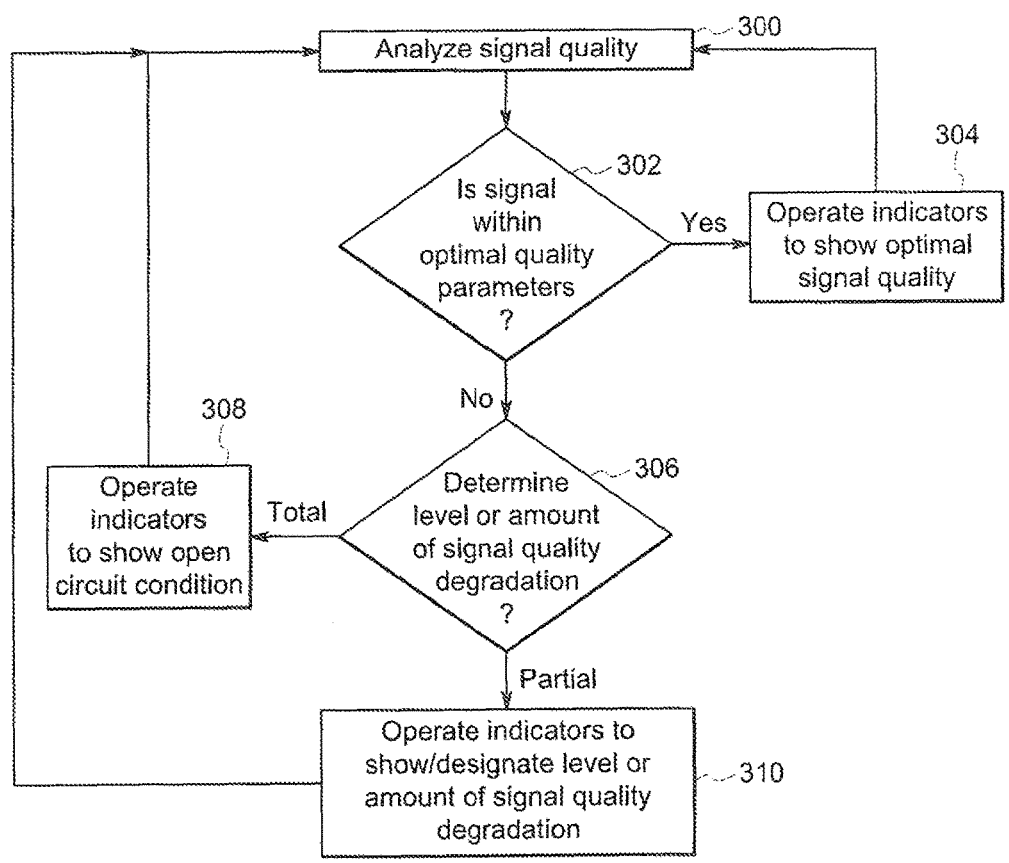
FIG. 3 is a schematic view of a method of operation of the signal quality indication system according to another exemplary embodiment of the invention.

Looking now at the illustrated exemplary and non-limiting embodiment of the method of operation of the device or system 200 in FIG. 3, the device or system 200 initially analyzes the signals coming from the cable lead 214 in block 300. In block 302, when the CPU 208 determines that the signal quality from a given cable lead 214 is within appropriate parameters, e.g., is present and has not degraded, in block 304 the CPU 208 can either operate the indicators 220 to provide this information to the physician, such as by emitting an "OK" signal from the indicators 220, or by not operating the indicators 220 in any manner, also providing the necessary information to the physician through the non-operation of the indicators 220. The mode of operation of the indicators 220 to provide the information to the physician confirming proper contact of the electrode 202 with the patient can take various forms that have a distinctive manner and/or color depending upon the particular scheme of operation of the indicators 220 to present information on the signal quality using the system 220. In one exemplary embodiment, the "OK" indication can be provided by operating the indicators 220 to emit a green light.

In block 302, if the CPU 208 analyzes the signal from a cable lead 214 in block and determines the signal quality, e.g., the impedance of the signal, is outside of the normal or optimal parameters, the CPU 208 determined the level of signal degradation in block 306. If no signal is present, whether due to a disconnection of the cable lead 214 from the electrode 202, the electrode 202 from the patient, or a failure in the cable lead 214 itself, in block 308 the CPU 208 can operate the indicators 220 in a manner indicating the failure of the signal on that cable lead 214. The form or manner of operation of the indicators 220 in this situation can have various forms, such as emitting light from the indicators 220 in a different color from the color utilized to indicate a proper signal quality discussed previously, e.g., operating the indicators 220 to emit a red light. In another exemplary and non-limiting embodiment, this indication can take the form of intermittently operating or flashing the indicators 220, optionally in a distinctive color as well, to provide information to the physician regarding the failure of the signal for that cable lead 214.

Alternatively, if in block 306 the CPU 208 detects that the signal from a cable lead 214 is present but is degraded in quality, such as due to imperfect contact of the electrode 202 with the patient 1000 or for any other reasons, in block 310 the CPU 208 can cause the indicators 220 to be operated in a manner representative of the amount or level of degradation in the signal, e.g., the impedance level of the signal. For example, the CPU 208 can operate the indicators 220 to emit different colors of light depending upon the level of degradation of the signal quality determined, with the differing colors emitted specifying the level of signal degradation to the physician. As discussed previously, the transition points or thresholds (e.g., signal noise levels) for the various signal degradation levels may be user selectable and thus determined at the discretion of the user, or the defaults supplied originally in the device or system 200 may be used to determine the exact nature of the operation of the indicators 220.

In an alternative exemplary embodiment, to illustrate the amount of degradation in the signal the CPU 208 can operate a different number of the indicators 220 on the cable lead 214, with each indicator 220 specifying a portion of the overall quality of the signal. Thus, by operating a number of the indicators 220 corresponding to the quality of the signal, the indicators 220 can provide a direct representation of the quality of the signal on the cable lead 214 to the physician.

In one exemplary embodiment, the indicators 220 take the form of an array 228 of spaced light sources 222 disposed either on the cable head 226 of the cable lead 214 immediately adjacent thee electrodes 202 or on the harness 216 adjacent and in alignment with the associated cable lead 214. For the indication of proper signal quality, as determined by the CPU 208, all of the light sources 222 are operated to each emit green light, signifying proper contact of the electrode 202 connected to the particular cable lead 214 with the patient 1000. In the situation where the signal quality is determined to be degraded due to imperfect contact of the electrode 202 with the patient 1000, the CPU 208 operates less than all of the light sources 222 to emit green light, with the number of light sources 222 being operated corresponding directly to the signal quality level transition threshold specified by the user or the device or system 200, i.e., the signal quality corresponding to the level/amount of contact of the electrode 202 with the patient 1000. Additionally, in the situation where the electrode 202 has become disconnected from the patient 1000, the CPU 208 can operate the light sources 222 to emit a red light and option to flash intermittently while emitting the red light to signify the disconnection of the electrode 202 from the patient 1000.

In an alternative and exemplary embodiment, in certain ECG monitoring applications, such as those disclosed in US Patent Application Publication No. US2015/0011901, entitled System And Method For Optimizing Electrocardiography Study Performance, the entirety of which is expressly incorporated herein by reference in its entirety for all purposes, the system or device 200 employs certain leads 214 to introduce a signal into the patient 1000, such as when a right leg drive (RLD) circuit (not shown) is utilized to provide a noise reduction by canceling common mode noise from the electrodes 202. When a circuit of this type is utilized with the system 200, the cable lead 214 employed to carry the signal to the RLD electrode 202 can also include the indicators 220. However, instead of providing an indication of the signal quality of a signal being received from the patient 1000 via the electrode 202 associated with the cable lead 214, in this exemplary embodiment the indicators 220 are operate to provide an indication of the state of the aggressive or incoming signal being transmitted to the patient 1000 via the RLD electrode 202. This, in turn, provides the physician with an indication of the level of the RLD signal being supplied to the patient 1000, optionally in the same manner as described in the prior exemplary embodiment, i.e., with all green indicators 220 evidencing an optimal quality RLD signal, a number of illuminated green indicators 220 less than the full number of indicators 220 evidencing a degraded RLD signal, and all red or red flashing indicators 220 evidencing a loss of connection of the RDL electrode 202 with the patient 1000.

In another exemplary embodiment, the step of determining the signal quality of the physiological signal transmitted by the cable lead 214 in block 302 can be accomplished by determining an amplitude of voltage noise at a power line frequency e.g., 50 Hz or 60 Hz, as well as harmonics of a power line frequency from an electrocardiogram signal transmitted by the cable lead 214 from the patient to the EP device 200.

With the device or system 200 including the indictors 220 on the cable leads 214 or harness 216 to provide a readily viewable indication of the signal quality to the physician, there is provided:

1. a significantly reduced amount of time wastage in the EP Lab through undetected bad electrode contact with the patient;

2. a much quicker assessment of electrode and cable lead connection quality without having to operate or review controls on the CPU; and 3. a much quicker assessment of any degrading performance over time in the electrodes and/or cable leads, such that either or both issues can easily observed and readily rectified.

In addition, from a technical perspective, the device or system 200 including the indicators 220 provides the ability to the physician to perform:

1. in process or study quality control on lead formation by detecting and correcting improper or imperfect electrode contact;

2. rapid identification of cable lead failure relative to the electrode site;

3. the ability to readily observe degradation of electrode contact over time;

4. the capability for user determined sensitivity levels;

5. a scaled analog interpretation of the electrode contact quality provide a readily discernable indication of signal quality.

In another exemplary embodiment, in addition or as a separate function from the signal relating to the quality of the signal, the indicators 220 can be operated to provide a visual indicator matching the color utilized to illustrate electrocardiogram traces (not shown) on the display 210,212 for the recording system 200. For example, when the recording system 200 is highlighting a particular cable lead 214/electrode 202 causing that electrocardiogram trace to be illustrated in a highlighting color (e.g., and orange or other readily visible color) to draw attention to the information relating to the particular signal coming from or going to that cable lead 214/electrode 202, the corresponding lead indicators 220 may display or emit the same color as on the display 210,212 to provide direct visual correlation between the cable lead 214/electrode 202 that is the origin of the signal from the patient and the information being highlighted on the display 210,212.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A signal quality indication system for actively indicating a signal quality associated with an electrocardiogram (ECG) signal transmitted via a cable lead and associated electrode operably connected to electrophysiology (EP) recording or mapping device, the signal quality indication system comprising:
   a central processing unit (CPU) configured to determine a signal quality of the ECG signal by determining: (i) an impedance of an electrocardiogram signal transmitted by the cable lead from the patient to the EP device, or (ii) an impedance of a right leg drive signal transmitted by the cable lead to the patient from the EP device, or (iii) an amplitude of voltage noise at power line frequency and harmonics of power line frequency from an electrocardiogram signal transmitted by the cable lead from the patient to the EP device;
   a cable lead including a first connector at one end configured to operably connect the cable lead to an electrode and a second connector at the opposite end configured to connect the cable lead to the CPU within the EP recording or mapping device; and
   an indicator disposed on the cable lead, wherein the indicator comprises a light source operated by the CPU to emit visible light having different levels of intensity and/or colors, each of the levels of intensity and/or colors associated with a different level of degradation of the signal quality of the ECG signal.

2. The signal quality indication system of claim 1 wherein the indicator is a multi-chromatic light source.

3. The signal quality indication system of claim 2 wherein the indicator is a multi-chromatic light emitting diode (LED).

4. The signal quality indication system of claim 1 wherein the indicator is an array of spaced light sources.

5. The signal quality indication system of claim 1 wherein the indicator is disposed on a cable head for the cable lead.

6. The signal quality indication system of claim 1 wherein the cable lead comprises:
   a harness;
   a connector cable extending from one end of the harness and configured to connect the harness to the EP recording or mapping device; and
   a number of cable leads connected to the harness opposite the connector cable.

7. The signal quality indication system of claim 6 further comprising a number of indicators, each indicator associated with one cable lead.

8. The signal quality indication system of claim 7 wherein the number of indicators are each disposed on the associated cable lead.

9. The signal quality indication system of claim 7 wherein the number of indicators are each disposed on the harness in alignment with the associated cable lead.

10. The signal quality indication system of claim 1, wherein the CPU is within the EP device.

11. An electrophysiology (EP) EP device for obtaining and recording information on a patient connected to the EP system, the EP device comprising:
    an amplifier including an electrode cable lead connector;
    a computer operably connected to the amplifier and including a central processing unit (CPU) connected to the amplifier;
    at least one cable lead connected to the cable lead connector and configured to supply a physiological signal to the CPU via the input module and amplifier, wherein the CPU is configured to determine a signal quality for the physiological signal supplied by the at least one cable lead by determining: (i) an impedance of an electrocardiogram signal transmitted by the cable lead from the patient to the EP device, or (ii) an impedance of a right leg drive signal transmitted by the cable lead to the patient from the EP device, or (iii) an amplitude of voltage noise at power line frequency and harmonics of power line frequency from an electrocardiogram signal transmitted by the cable lead from the patient to the EP device; and
    an indicator disposed on the at least one cable lead, wherein the indicator comprises a light source operated by the CPU to emit visible light having different levels of intensity and/or colors, each of the levels of intensity and/or colors associated with a different level of degradation of the signal quality of the physiological signal determined by the CPU.

12. The EP device of claim 11 wherein the at least one cable lead comprises:
    a harness including a connector cable operably engageable with the cable lead connector;
    a number of cable leads operably connected to the harness; and
    a number of indicators disposed on one of the harness in association with each of the cable leads or each of the number of cable leads.

13. The EP device of claim 12 wherein the number of indicators each include an array of spaced light sources.

14. The EP device of claim 13 wherein each light source is a multi-chromatic light emitting diode (LED).

15. The EP device of claim 14 wherein the CPU is configured to operate each multi-chromatic LED to emit light of different intensities from various diodes forming the LED.

16. A method of providing an indication of a quality of an physiological signal transmitted between an electrode disposed on a patient and an electrophysiology (EP) recording or mapping device, the method comprising the steps of:
    a) providing a signal quality indication system operably connected to a central processing unit (CPU) of the EP device, the signal quality indication system including a cable lead and a light source disposed in the cable lead and operably connected to the CPU, wherein the light source is operated by the CPU to emit light corresponding to a determination of the signal quality of the physiological signal;
    b) connecting the cable lead between the electrode and the CPU;
    c) determining the signal quality of the physiological signal transmitted by the cable lead by determining: (i) an impedance of an electrocardiogram signal transmitted by the cable lead from the patient to the EP device, or (ii) an impedance of a right leg drive signal transmitted by the cable lead to the patient from the EP device, or (iii) an amplitude of voltage noise at power line frequency and harmonics of power line frequency from an electrocardiogram signal transmitted by the cable lead from the patient to the EP device; and d) operating the light source to emit visible light having different levels of intensity and/or colors, each of the levels of intensity and/or colors associated with a different level of degradation of the physiological signal.

17. The method of claim 16 wherein the light source comprises an array of spaced light sources, and wherein step of operating the light source comprises the step of operating one or more of the array of light sources in correspondence with a determined quality of the physiological signal.

18. The method of claim 16 wherein the step of operating the light source further comprises the step of flashing the light source.

19. The method of claim 16 further comprising:

matching an electrode disposed on a patient with a highlighted illustration of a signal from the electrode on an electrophysiology (EP) recording or mapping device by:

determining an origin of a physiological signal being highlighted on a display; and operating the light source on the cable lead associated with the electrode that is the origin of the physiological signal to emit a color corresponding to a color of the highlighted signal on the display.

* * * * *